United States Patent
Ramsbottom (10) Patent No.: US 6,560,013 B1
(45) Date of Patent: May 6, 2003

(54) ENDOSCOPE WITH VARIABLE DIRECTION OF VIEW

(75) Inventor: Andrew Paul Ramsbottom, Westcliff on Sea (GB)

(73) Assignee: Keymed (Medical & Industrial Equipment) Ltd., Southend-on-Sea (GB)

( * ) Notice: Subject to any disclaimer, the term of this patent is extended or adjusted under 35 U.S.C. 154(b) by 0 days.

(21) Appl. No.: 10/019,629
(22) PCT Filed: Aug. 2, 2000
(86) PCT No.: PCT/GB00/02980
§ 371 (c)(1),
(2), (4) Date: Jan. 3, 2002
(87) PCT Pub. No.: WO01/22865
PCT Pub. Date: Apr. 5, 2001

(30) Foreign Application Priority Data

Sep. 28, 1999 (GB) .............................................. 9922960

(51) Int. Cl.⁷ .............................. G02B 21/06; G02B 5/04
(52) U.S. Cl. ........................ 359/431; 359/362; 359/385; 359/831
(58) Field of Search ................................. 359/362, 368, 359/431, 831–837; 600/109–117, 173–174; 348/65, 82–85

(56) References Cited

U.S. PATENT DOCUMENTS

| | | | | |
|---|---|---|---|---|
| 3,880,148 A | * | 4/1975 | Kanehira et al. ............ 600/173 |
| 4,398,811 A | * | 8/1983 | Nishioka et al. ............ 359/831 |
| 4,500,181 A | | 2/1985 | Takahashi .................... 359/385 |
| 4,671,630 A | | 6/1987 | Takahashi .................... 359/385 |
| 4,697,577 A | * | 10/1987 | Forkner ......................... 128/6 |

FOREIGN PATENT DOCUMENTS

| | | |
|---|---|---|
| DE | 299 07 430 | 9/1999 |
| EP | 0 251 478 | 1/1988 |
| WO | WO 99/00642 | 1/1999 |
| WO | WO 99/42028 | 8/1999 |

OTHER PUBLICATIONS

Olympus Industrial "Borescopes, OES Swing–Prism Borescope" (2 pages), believed to be Mar. 1990, (Olympus Optical Co. Ltd.).

Patent Abstract of Japan, vol. 018, No. 619 (C–1278) Nov. 25, 1994 & JP 06 237881 A (Olympus Optical Co Ltd), Aug. 30, 1994.

* cited by examiner

*Primary Examiner*—Thong Nguyen
(74) *Attorney, Agent, or Firm*—Smith, Gambrell & Russell (57) ABSTRACT

An endoscope includes an optical train or image-to-video conversion device, defining a longitudinal axis, for receiving an image for transmission to a viewing device. A first prism having a reflective surface at 45° to the longitudinal axis and laterally offset from is mounted for rotation about an axis that is perpendicular to and intersecting the longitudinal axis and the axis intersecting the center of the reflective surface. A second prism with a reflective surface at 45° to and intersecting the longitudinal axis is also provided. The field of view is illuminated by light transmitted to a third prism with a reflective surface mounted symmetrically about the longitudinal axis with respect to the first reflector and rotatable synchronously with the first reflector. In this way, the direction of view and of illumination can an be varied synchronously over a range of about 120°.

20 Claims, 10 Drawing Sheets

ENDOSCOPE WITH VARIABLE DIRECTION OF VIEW

FIELD OF THE INVENTION

The present invention relates to an improved swing prism arrangement for varying the direction of view in a borescope or endoscope.

BACKGROUND OF THE INVENTION

Borescopes and endoscopes are well known devices for viewing features at remote or inaccessible locations, such as within complex machinery or within the human body. Many such devices are provided with a rotatable prism (a so-called "swing prism") at the distal end of the device to provide a continuously variable direction of view. Typically, the maximum range of variation in direction of view which can be obtained is in the region of 70° and it is usually necessary to provide different scopes for forward and lateral viewing.

BRIEF SUMMARY OF THE INVENTION

The present invention provides apparatus for use as a borescope or endoscope, comprising a tube having a proximal end and a distal end; a viewing port at the distal end; means in the tube for receiving a image of a viewed field through the viewing port for transmission to a viewing device, the image receiving means defining a longitudinal axis; a first reflector having a reflective surface mounted at 45° to the longitudinal axis and laterally offset therefrom, and mounted for rotation about a rotation axis perpendicular to and intersecting the longitudinal axis and intersecting the centre of the reflective surface; a second reflector having a reflective surface mounted at 45° to the longitudinal axis and intersected by the longitudinal axis, such that light entering the viewing port is reflected by the first reflector to the second reflector and by the second reflector into the image receiving means; and further comprising means to illuminate the viewed field, comprising means to transmit light to a third reflector in the distal end of the tube and having a reflective surface mounted symmetrically about the longitudinal axis with respect to the first reflector and rotatable synchronously with the first reflector about the rotation axis.

The means for receiving an image may comprise a plurality of lenses for transferring the image from the distal to the proximal end of the tube. In this case, the viewing device may comprise an eyepiece assembly at the proximal end of the tube.

Alternatively, the means for receiving the image may comprise an image-to-video conversion device. In this case, the viewing device may comprise a screen for displaying a video image.

The means to transmit light conveniently comprises a bundle of optical fibres and at least one light guide and/or at least one right-angle prism.

In one embodiment, the means to transmit light includes three right-angled prisms.

The means to transmit light may include a right-angle prism mounted such that its hypotenuse face is adjacent the back of the first reflective surface.

In the apparatus, one or more of the first, second and third reflectors typically comprise a right-angle prism.

The apparatus may further comprise means to prevent rotation of the viewed image as the first reflector rotates about the rotation axis.

When the image receiving means comprises an image-to-video conversion device, it may be mounted to rotate synchronously with the first reflector to prevent rotation of the viewed image.

Alternatively, the means to prevent rotation of the viewed image may comprise a dove prism, a double dove prism or a Pechan prism.

In this case, the apparatus preferably also comprises means to correct inversion of the image produced by the rotation preventing prism(s).

The means to correct inversion of the image may also comprise a dove prism, a double dove prism or a Pechan prism.

The invention also provides apparatus for use a borescope or endoscope, comprising a tube having proximal and distal ends, a viewing port at the distal end, means to gather an image of a viewed field through the viewing port for transmission to a viewing device and means to illuminate the viewed field, comprising a plurality of optical fibres for transmitting light through the tube to the distal end, a reflector operable to reflect light from the fibres out of the tube, and means to transmit light from the fibres to the reflector comprising at least one light guide and/or at least one right-angled prism.

Preferably, the reflector is rotatably mounted and may comprise a right-angled prism.

Preferably, each light guide and/or right-angled prism in the means to transmit light is spaced from each adjacent light guide or prism by a spacing greater than approximately 1 wavelength.

BRIEF DESCRIPTION OF THE FIGURES

The invention will now be described in detail, by way of example only, with reference to the accompanying drawings in which:

FIG. 6b shows an end view of a scope tip of FIG. 6a in which the prisms 18 and 20 have been rotated around the axis R through approximately 120° as compared with the position shown in FIG. 6a;

DETAILED DESCRIPTION OF THE INVENTION

Figure 1A:
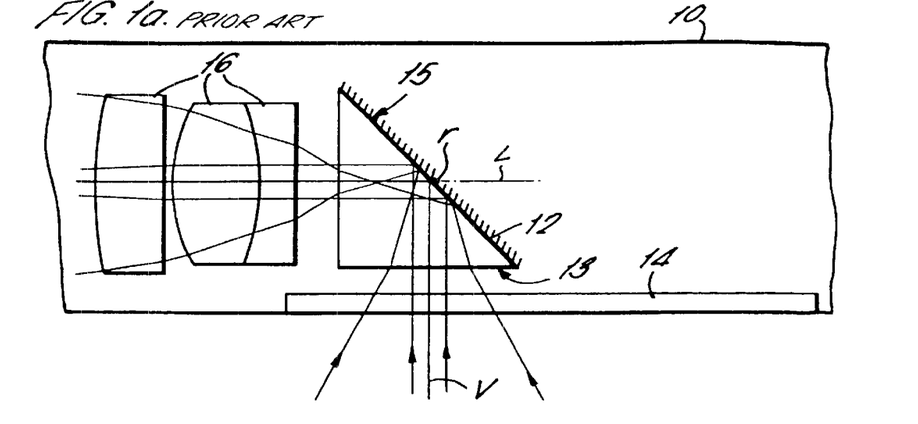
FIGS. 1a–1c are schematic views of a prior art swing prism arrangement in the distal end of a borescope or endoscope.
Figure 1B:
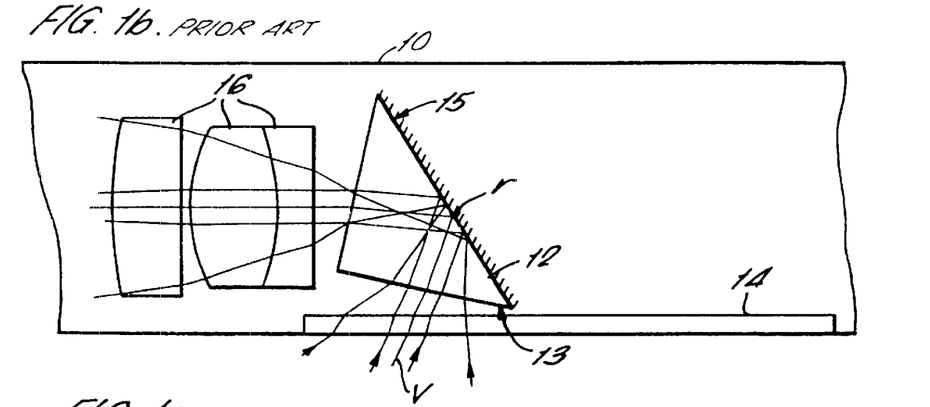
Figure 1C:
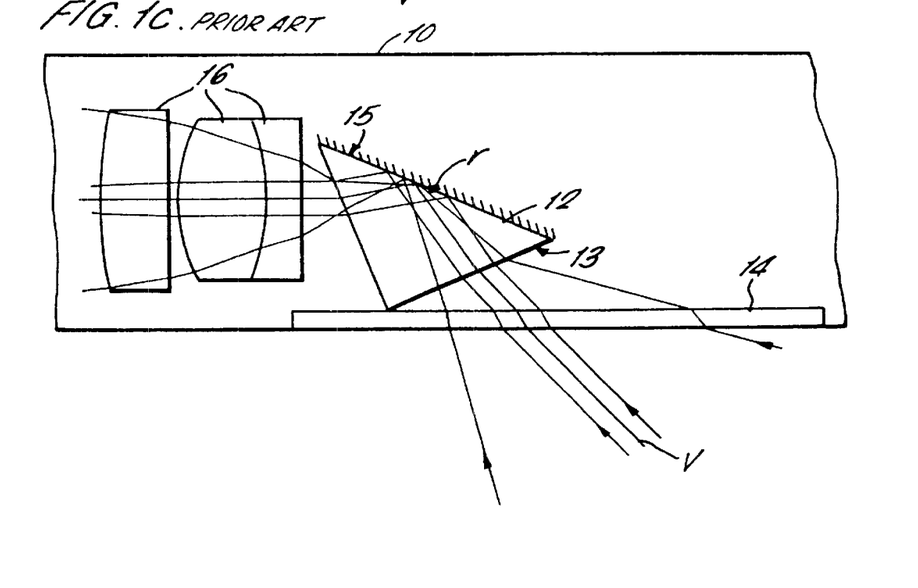

FIG. 1a is a schematic view of a conventional swing prism arrangement in the distal tip of a borescope or endoscope 10. A right-angle prism 12 reflects light received through a viewing window 14 into an optical train 16 for transmission to the proximal end of the scope 10 (or through an imaging lens directly on to an image-to-video conversion device such as a CCD chip for transmission to a video screen). The direction of view (DOV) is the angle between the longitudinal axis L defined by the image receiving components in the scope 10, which may be a relay of lenses forming an optical train 16 as shown or an image-to-video conversion device such as, a CCD chip, and the viewing axis V defining the center of the field of view (FOV). In FIG. 1a, the direction of view is 90°. However, the prism 12 is rotatably mounted for rotation about an axis r perpendicular to the plane of the paper so that it can be tilted as shown in FIGS. 1b and 1c in order to change the direction of view.

The range of DOV variation achievable by such a mechanism is limited fundamentally by the size of the prism 12 in relation to the optical ray footprint through the prism 12 (the optical ray footprint being the area occupied by the bundle of light rays at a given surface). As the prism 12 is tilted, the angular shift in DOV is twice as large as the actual angular change in orientation of the prism 12. Hence, as the prism rotates, the optical ray footprint on the prism entry face 13 shifts and will eventually be clipped by the edges of the prism 12.

In order to minimize the optical ray footprint at the prism 12, the optical system is usually designed such that the entrance pupil of the system falls at or near to the mirrored surface 15 of the prism 12. The entrance pupil of an optical system is the image of the limiting aperture as viewed in object space. In a borescope or endoscope, the entrance pupil is usually the part of the system where the optical rays occupy the smallest footprint. The size of the entrance pupil determines the amount of light collected by the system and is related to the maximum image brightness and/or image size presented by the scope. There is a trade off between the basic design parameters of the scope, i.e the entrance pupil size, prism size, field of view and the range of variation in DOV (sometimes referred to as the "swing range"). Generally, for any given size of prism 12, the achievable swing range will decrease as the field of view or the entrance pupil size increase.

Figure 2:
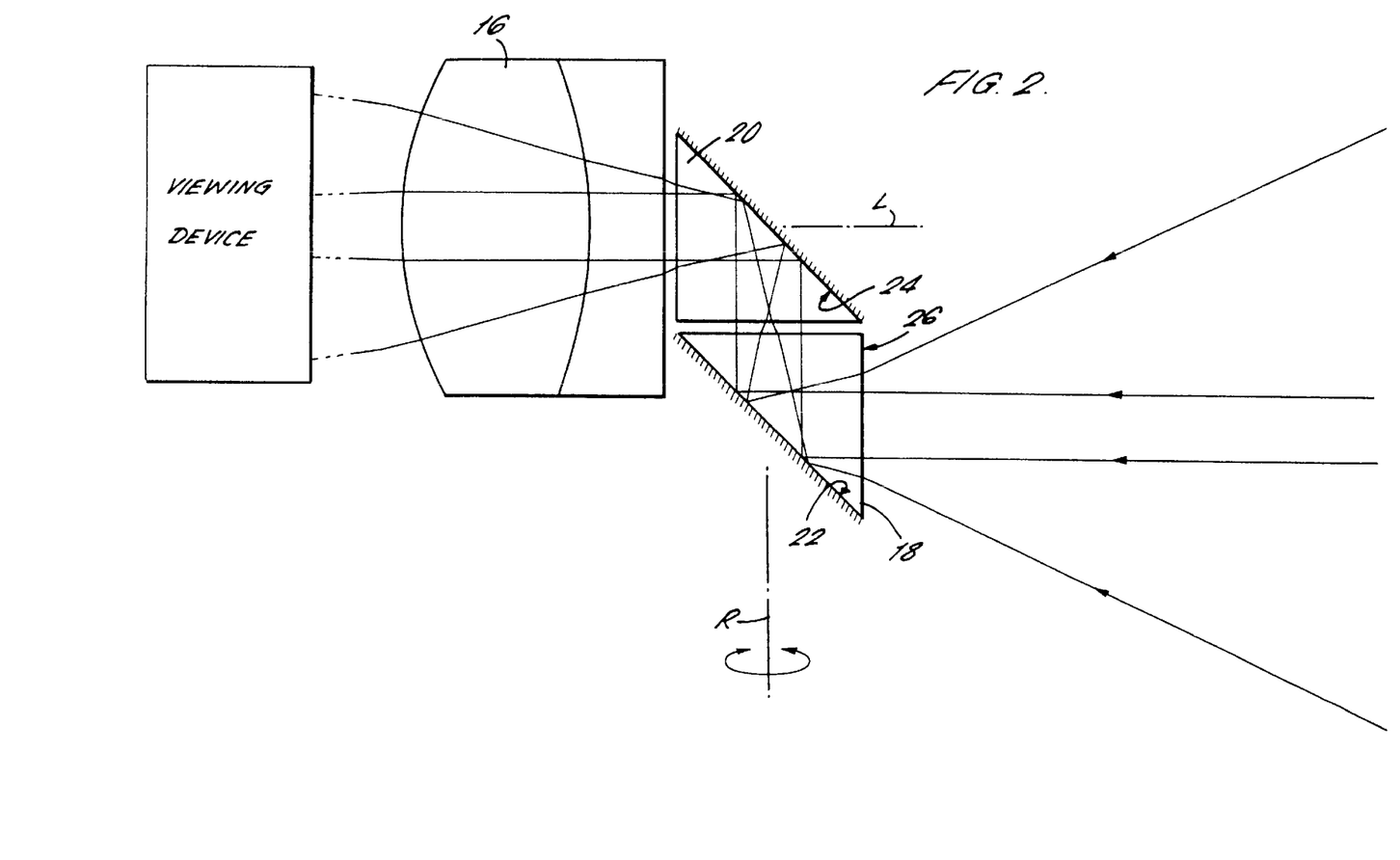
FIG. 2 is a schematic view of a swing prism arrangement in accordance with an embodiment of the present invention.
Figure 2A:
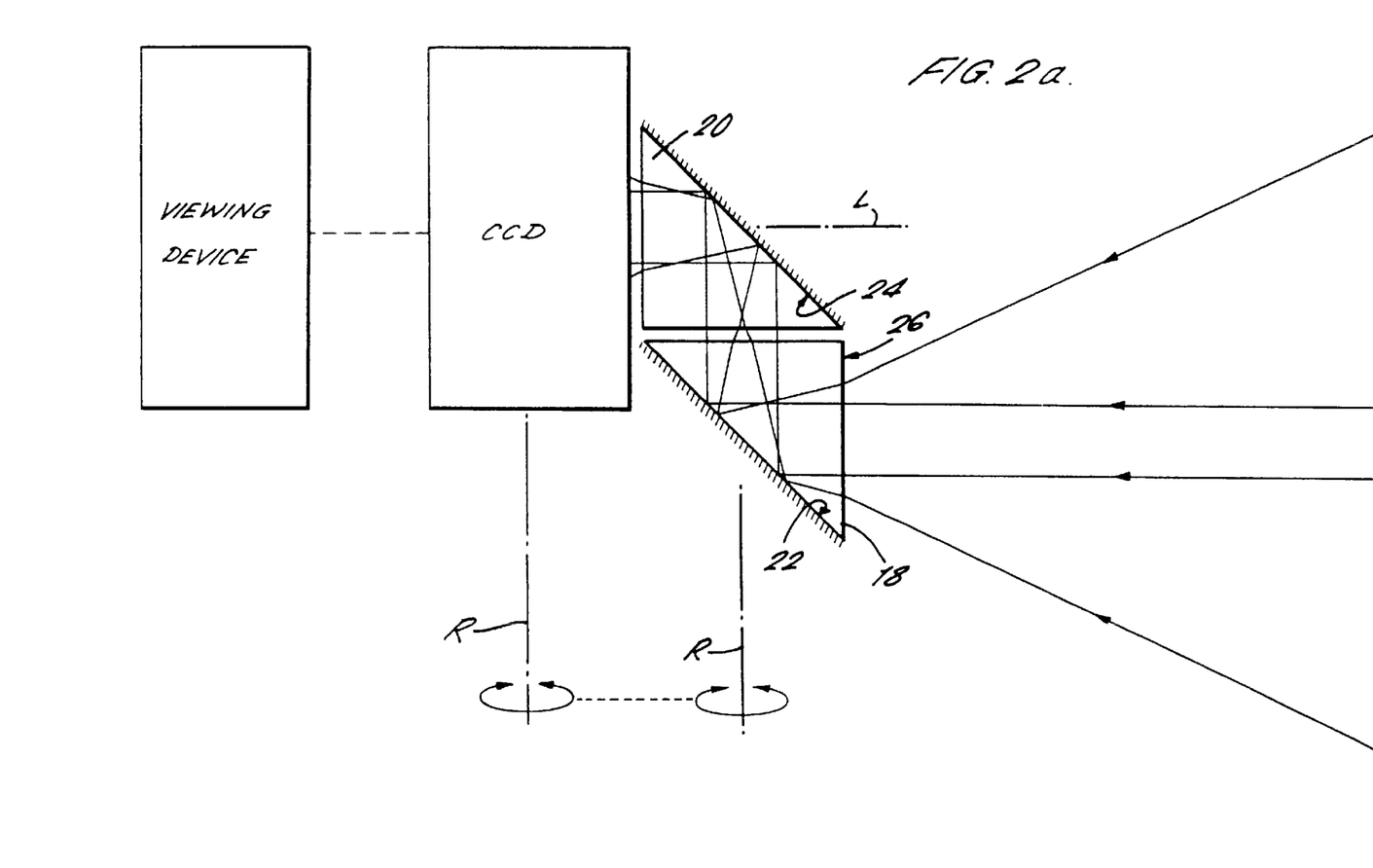
FIG. 2a is schematic view of a swing prism arrangement in accordance with another embodiment of the present invention.

A first embodiment of the present invention which achieves a larger range of variation in DOV is illustrated schematically in FIG. 2. In this case, two reflectors 18,20, such as two right-angle prisms with mirror coatings on their hypotenuse faces, are provided. The first prism 18 is mounted for rotation about an axis R which lies in the plane of the paper and intersects the reflective hypotenuse face 22 of the prism 18 at 45° and at its center point. The second prism 20 is fixed. In this way, light received by the first prism 18 is reflected from its hypotenuse face 22 into the second prism 20, and reflected by the hypotenuse face 24 of the second prism 20 into the optical train 16 (or imaging lens or CCD chip, as in FIG. 2a, etc.) of the scope 10.

The arrangement shown provides forward viewing, i.e a DOV of 0°. However, if the first prism 18 is rotated about the axis R then the DOV (measured in a plane perpendicular to the plane of the paper) and the direction of the light rays received through the entry face 26 of the prism 18 will also rotate out of the plane of the paper by exactly the same angle as the prism 18 itself rotates. In this way, the optical ray footprint through the prism 18 does not change as the prism 18 rotates.

Therefore, in this arrangement the swing range is no longer fundamentally limited by the size of the prism 18, which must now only be large enough to accommodate the entrance pupil size and field of view desired. The swing range achievable is now only limited by the mechanical arrangement and any obstructions in the tip of the scope 10.

The swing prism arrangement in accordance with the present invention allows a much wider range of variation in DOV than in conventional scopes. For example, a range of 0°–120° can easily be obtained, allowing both forward and lateral viewing by a single scope.

However, in order to use a borescope or endoscope in most environments it is necessary to illuminate the field of view (FOV). Typically, a bundle of optical fibres is provided in the scope to transmit light from a light source at the proximal end to the distal end of the scope, where it is projected out of an illumination port adjacent the viewing port. As the DOV changes the field of view may fall outside the field of illumination. Conventional swing prism scopes overcome this problem by splitting the bundle of optical fibres into a number of arms and directing each arm to project light over a different region of the DOV range. However, the wider the DOV range, the lower will be the luminous intensity of the illumination provided in each area and the corresponding brightness in the viewed image will decrease.

In accordance with the present invention, this limitation can be avoided by varying the direction of the illumination such that it is always coincident with the direction of view.

Figure 3:
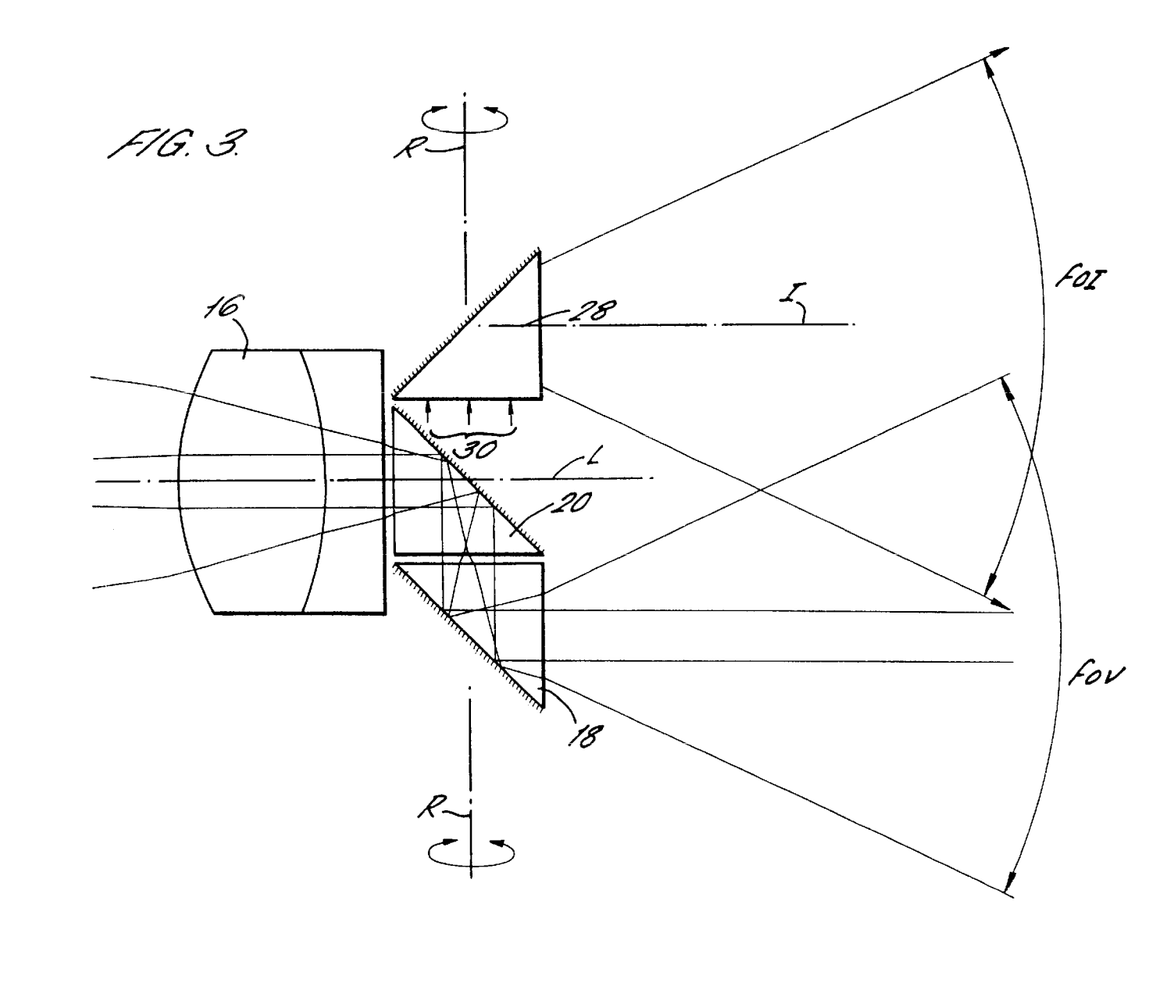
FIG. 3 is a schematic view of the swing prism arrangement of FIG. 2 further including means to provide directional illumination.

FIG. 3 is a schematic diagram of an embodiment in which the illumination axis I, defining the center of the illumination projected out of the scope, is variable synchronously with the direction of view. Here, a third prism 28 receives light from transmission means (as discussed further below) and reflects it out of the scope 10 as shown. The third prism 28 is symmetrically placed about the longitudinal axis L with respect to the first prism 18 and is linked to the first prism 18 such that they rotate synchronously about the same axis R, thereby directing light in the same direction as the DOV. Although the field of view FOV and the field of illumination FOI are laterally offset from one another as shown, within a few millimetres from the scope 10 the two overlap so that in practice the field of view will be illuminated.

In order to provide light into the third prism 28 in the direction of arrows 30, light is transmitted through the scope 10 by a bundle of optical fibres (not shown in FIG. 3) in a direction generally parallel with the longitudinal axis L. This light must then be redirected round at least one 90° bend in order to enter the third prism 28. It is not possible within the confines of a typical borescope with a diameter of, say, 5 mm to bend the optical fibres themselves around such an angle. However, this can be accomplished by means of a series of light guides and right-angled prisms as illustrated in FIG. 4.

Light from a bundle of optical fibres (not shown) can be coupled directly into a conventional light guide of rectangular cross-section 34. Light entering the light guide 34, whether from a fibre at the center of the bundle or from a fibre at the edge of the bundle, and even when the light is directed at a relatively large angle θ to the direction of the fibre, is efficiently contained by means of total internal reflection from the side walls of the light guide 34. Light exiting the light guide can be turned through 90° by means of a right-angled prism 36 and into a second light guide 38. The prism 36 must be placed as close as possible to the ends of the two lights guides 34,38 without touching. The small gap 9 (greater than about one wavelength) is necessary in order to preserve the total internal reflection at the surface.

Figure 4:
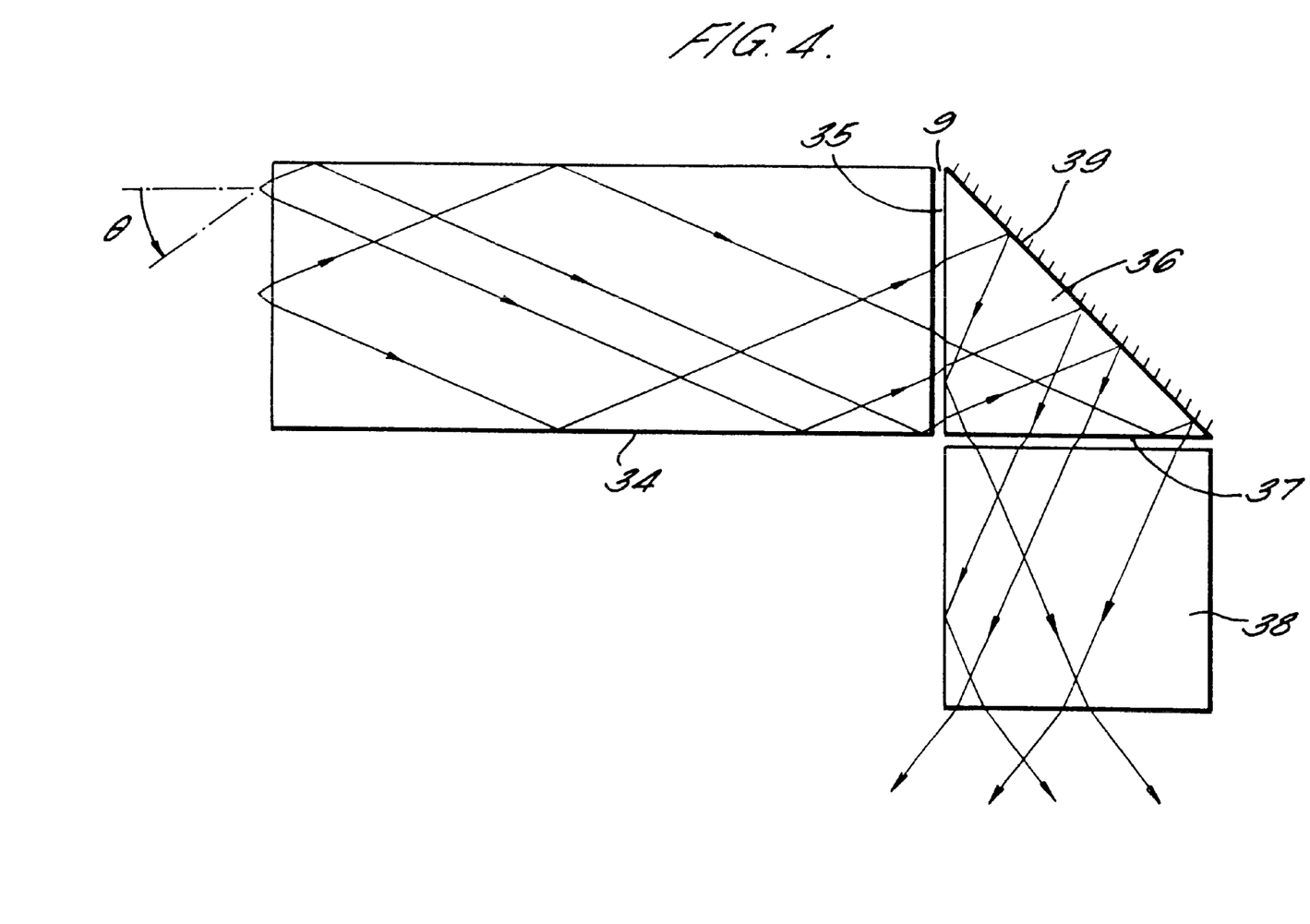
FIG. 4 is a schematic view of a light guide arrangement to divert light through 90°.

As can be seen in FIG. 4, any light contained within the first light guide 34 is necessarily also contained within the prism 36 since the exit face 37 of the prism 36 can be considered as a continuation of the side wall of the first light guide 34, totally reflecting the incident light in the same way. The entrance face 35 of the prism 36 acts similarly to light which has been turned through 90° by reflection from the hypotenuse face 39.

Figure 5:
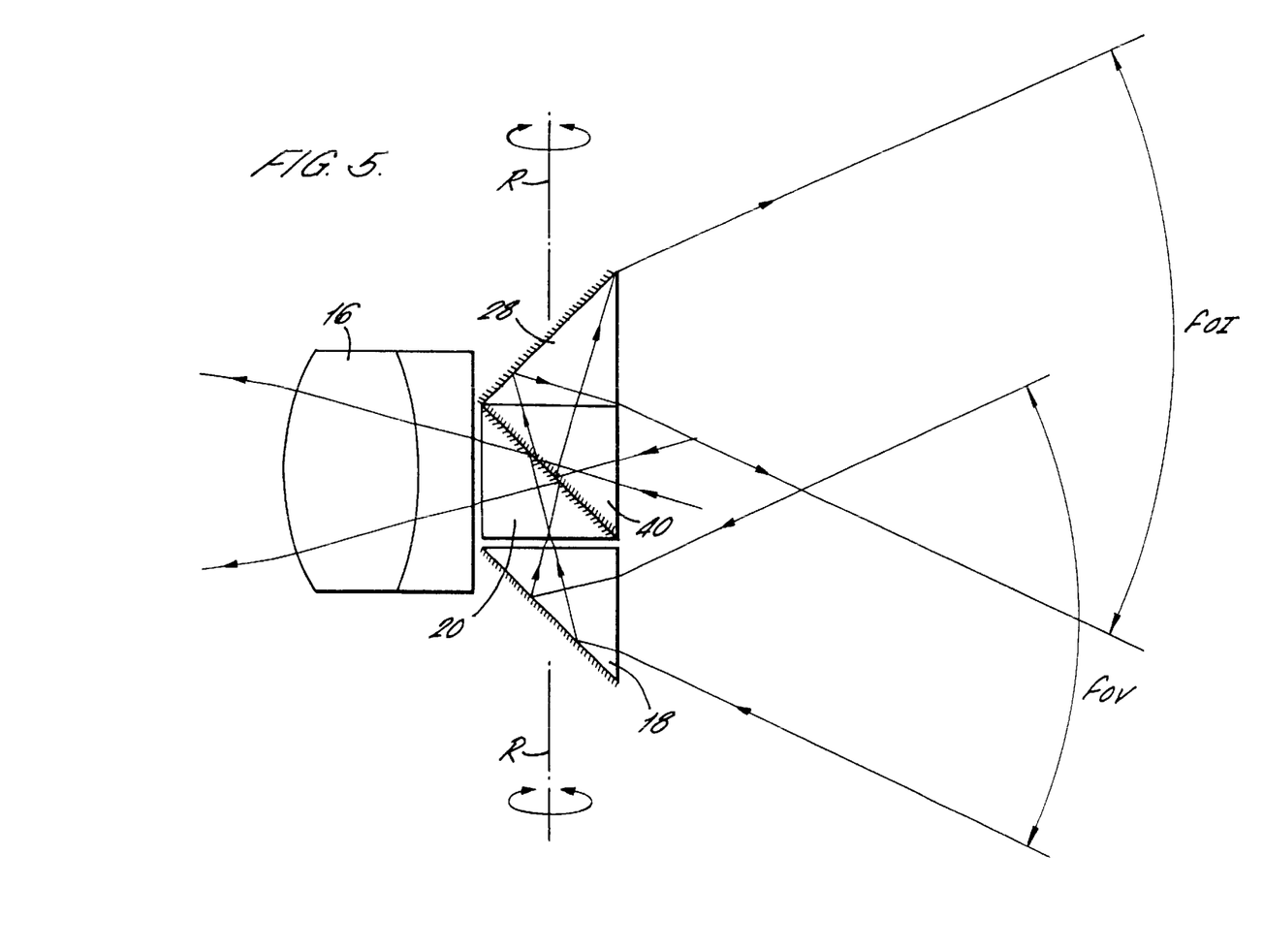
FIG. 5 is a schematic view of the arrangement in FIG. 3 with further details of the directional illumination.

In this way, a series of light guides and prisms can be used to manipulate the light, if necessary through a complex folded path. For example, light may be turned through 180° so as to enter a fourth prism 40 placed back to back with the fixed prism 20 as shown in FIG. 5. The fourth prism turns the light through a further 90° into the third prism 28. Since the illumination light is now directed from point at the same axial distance along the scope 10, as the prisms 18 and 20 which gather an image, it is possible to achieve a short tip length, i.e the length between the distal end of the scope 10 and the viewing window. This is advantageous for use in particularly confined spaces.

Figure 6A:
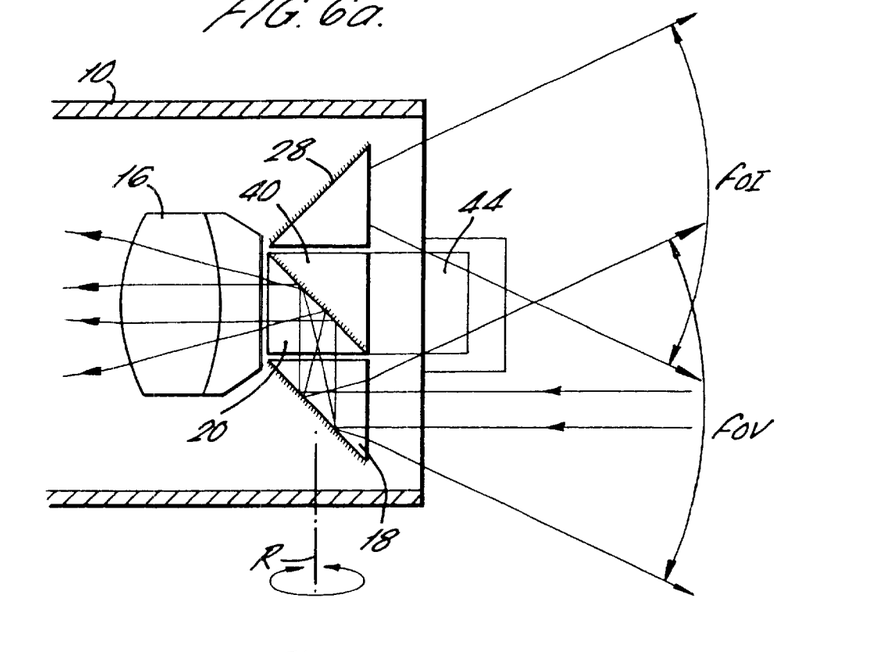
FIG. 6a shows a partially cross-sectioned view from above a scope tip.
Figure 6B:
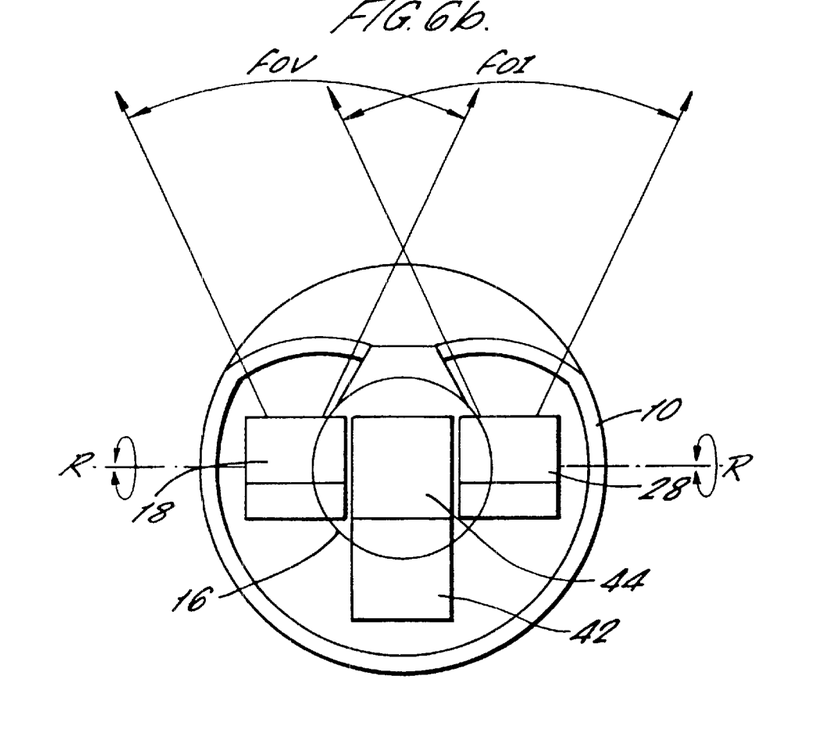
Figure 6C:
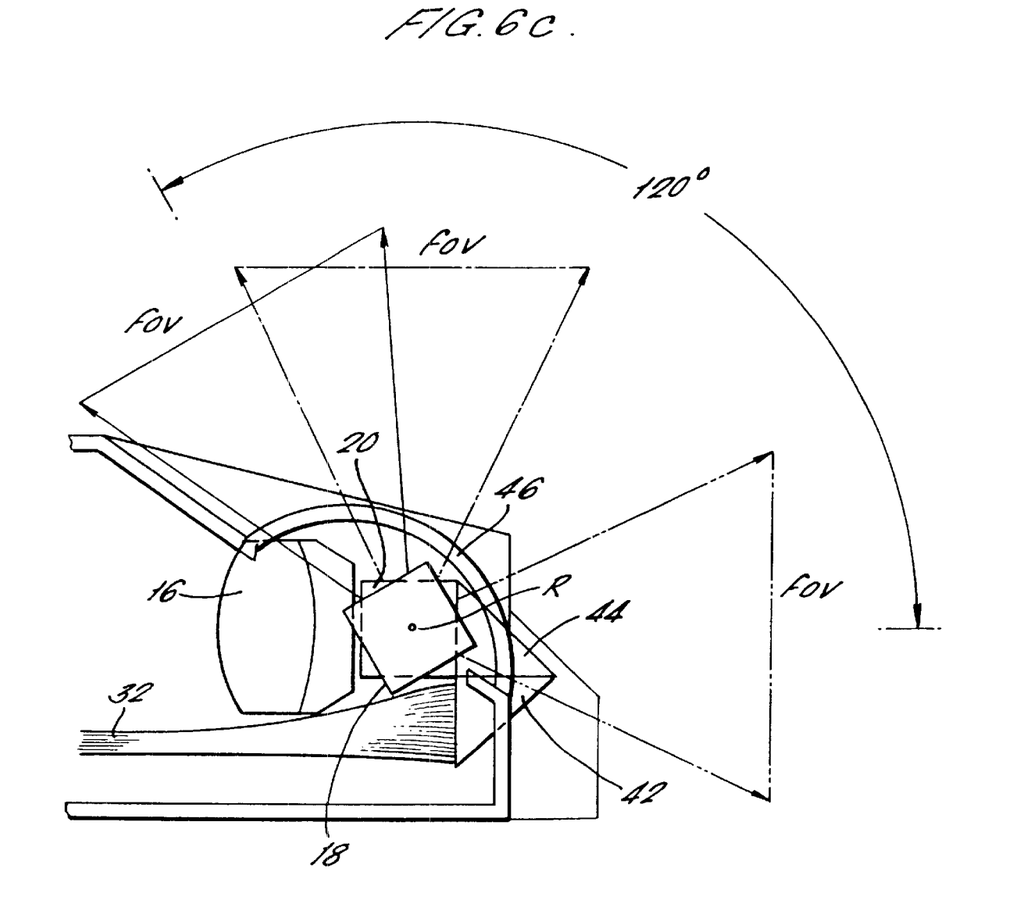
FIG. 6c shows a side view of the scope tip of FIG. 6b.

FIGS. 6a to 6c illustrate in schematic form how the present invention may be embodied within the tip of a scope 10. FIG. 6a shows a partially cross-sectioned view from above of the scope tip. FIGS. 6b and 6c respectively show an end view and a side view of the scope tip as in both cases the rotatable prisms 18 and 28 have been rotated about the axis R through approximately 120° as compared with their position shown in FIG. 6a.

As best seen in FIG. 6c, a bundle of optical fibres 32 is provided in the scope beneath the four prisms 18, 20, 40 and 28 and beneath the optical train 16. Two further fixed prisms 42 and 44 are provided to turn the light from the fibres 32 through 180° so as to enter the fourth prism 40. This fourth prism 40 diverts the light through 90° into the rotating prism 28. The rotating prism 28 again diverts the light through 90° so as to exit the scope through the viewing window 46. The viewing window 46 is preferably partially spherical so as to accommodate the rotating prisms and to allow a large swing range. As shown in FIG. 6c, this arrangement is able to accommodate a swing range of 120°. A DOV of 0° and 90° are shown in dotted lines for comparison.

In a conventional swing prism scope, because the light passes through only one right-angled prism the image suffers left-right inversion which needs to be corrected elsewhere in the scope. In the swing prism arrangement of the present invention, light received from a viewed object passes through two right-angled prisms 18, 20 and therefore the image entering the optical train 16 from the prism 20 does not suffer left-right inversion. However, the image will rotate as the rotatable prism 18 is moved. This image rotation may be removed in various ways.

For example, if the scope 10 includes a CCD chip and imaging lens (not shown) rather than an optical train 16 so that an image is provided from the fixed prism 20, through the imaging lens, directly on to the chip, then the chip itself may be arranged to rotate to compensate for rotation of the prism 18.

Figure 7A:
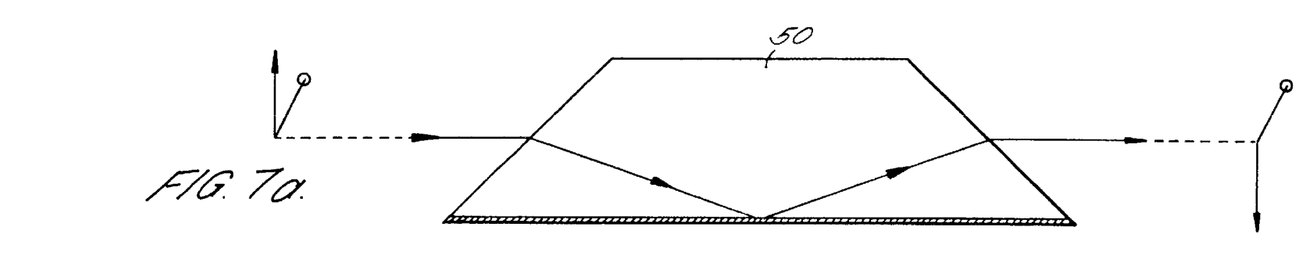
FIG. 7a shows an arrangement for correcting image rotation using a dove prism.
Figure 7B:
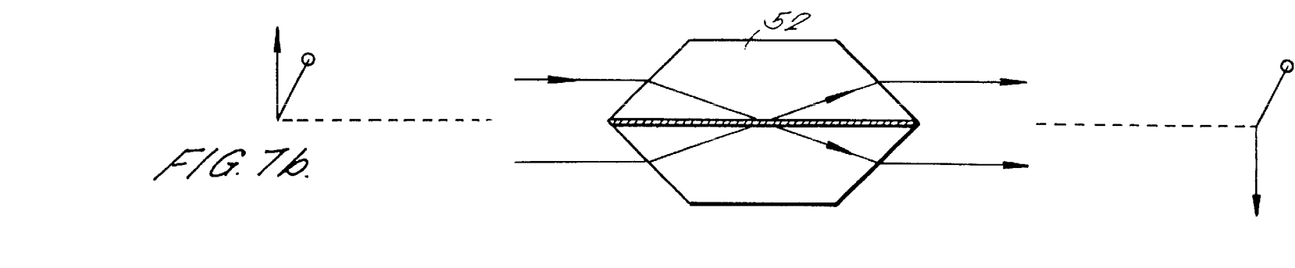
FIG. 7b shows an arrangement for correcting image rotation using a double dove prism.
Figure 7C:
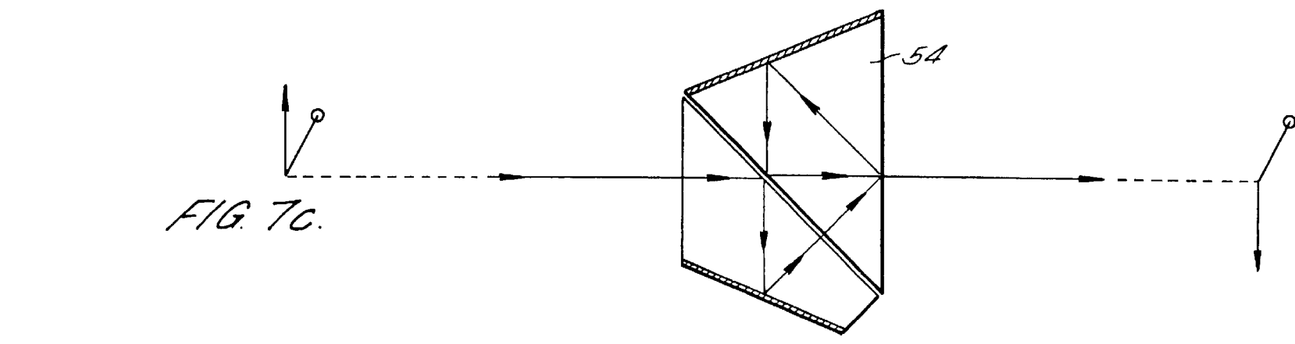
FIG. 7c shows an arrangement for correcting image rotation using a Pechan prism.

Alternatively, optical means may be provided for rotating the image. In a borescope using a conventional optical relay train 16, the rotation of the rotating prism 18 can be mechanically linked to a compensating rotation of a suitable image rotation prism which may be included either within the relay lens section or within the ocular assembly (not shown) at the proximal end of the scope 10. Suitable prism arrangements include a dove prism 50, double dove prism 52 and Pechan prism 54 as illustrated in FIGS. 7a–7c respectively. The dove and double dove prisms can only operate in parallel light and therefore must be positioned either in a parallel relay section or behind the ocular lens. The Pechan prism 46 can operate in divergent or convergent beams, therefore offering greater flexibility in its positioning within the system.

It will be appreciated that these three examples are not exclusive and many other arrangements well known in the art could be used to remove image rotation.

The use of any of these image de-rotation prisms necessarily results in an image inversion and therefore this must be removed by the presence of a second, non-rotating dove, double dove or Pechan prism elsewhere within the optical system.

Figure 8:
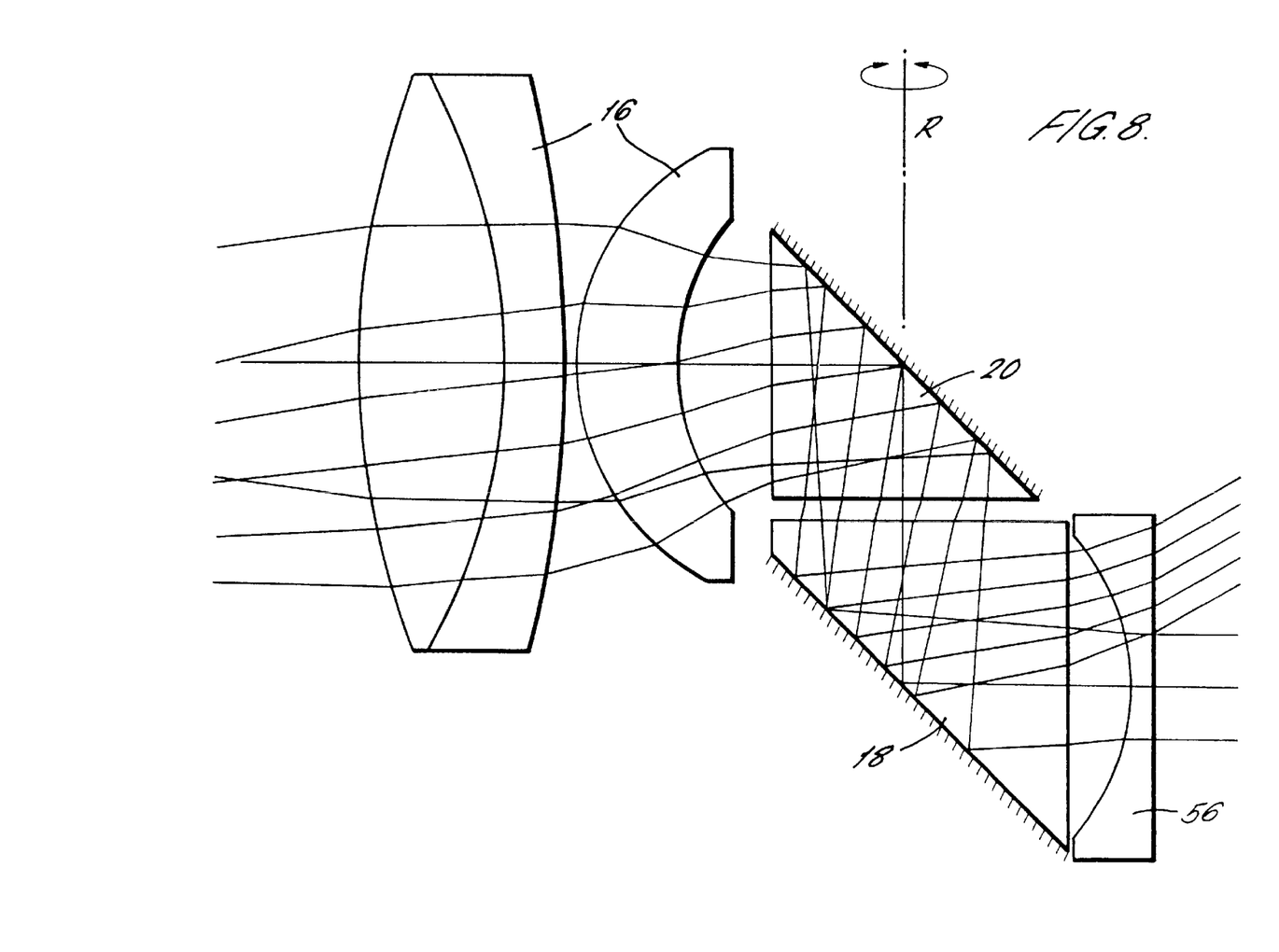
FIG. 8 is a schematic view of an arrangement as in FIG. 2 also including a retro focus lens system.

Another advantage of the system of the present invention is that it allows the use of a negative lens element in a retro-focus type design. Use of a negative lens element is common in fixed DOV systems in which large fields of view are required. The negative lens element serves to direct high obliquity, off-axis principal rays towards the effective aperture stop on the prism surface to maximise the amount of light captured by the prism and entering the optical system. This is not possible with a conventional swing prism scope, of the type illustrated in FIGS. 1a–1c, because as the prism 12 rotates the optical axis on the negative lens element shifts and leads to unacceptable optical aberrations. However, when a swing prism arrangement in accordance with the present invention is utilised then, as shown in FIG. 8, a negative lens element 56 can be placed in front of the entry face of the first rotating prism 18. If the negative lens element 56 is arranged to rotate with the prism 18 about the axis R then the optical axis on the negative lens element 56 does not shift. Thus, the amount of light entering the optical system and in the turn the image brightness achievable is increased.

As those skilled in the art will appreciate, the present invention provides an improved swing prism scope with a greatly increased variation in the achievable direction of view, thereby obviating the need for separate scopes for forward and lateral viewing. The means for altering the direction of illumination also ensures that an object anywhere within the variable field of view can be properly illuminated for effective viewing. It will also be apparent to the skilled reader that a number of modifications and variations are necessary to the precise details and configurations described herein without departing from the scope of the claims.

What is claimed is:

1. Apparatus for use as a borescope or endoscope, comprising:

a tube having a proximal end and a distal end;

a viewing port at the distal end;

means in the tube for receiving an image of a viewed field through the viewing port for transmission to a viewing device, the image receiving means defining a longitudinal axis;

a first reflector having a reflective surface mounted at 45° to the longitudinal axis and laterally offset therefrom, and mounted for rotation about a rotation axis perpendicular to and intersecting the longitudinal axis and intersecting the center of the reflective surface;

a second reflector having a reflective surface mounted at 45° to the longitudinal axis and intersected by the longitudinal axis, such that light entering the viewing port is reflected by the first reflector to the second reflector and by the second reflector into the image receiving means; and means to illuminate the viewed field, said means to illuminate including a third reflector and means to transmit light to the third reflector in the distal end of the tube, with said third reflector having a reflective surface mounted symmetrically about the longitudinal axis with respect to the first reflector and being rotatable synchronously with the first reflector about the rotation axis.

2. Apparatus as claimed in claim 1, wherein the means for receiving an image comprises a plurality of lenses for transferring the image from the distal to the proximal end of the tube.

3. Apparatus as claimed in claim 2, wherein the viewing device comprises an eyepiece assembly at the proximal end of the tube.

4. Apparatus as claimed in claim 1, wherein the means for receiving the image comprises an image-to-video conversion device.

5. Apparatus as claimed in claim 4, wherein the viewing device comprises a screen for displaying a video image.

6. Apparatus as claimed in claim 1, wherein the means to transmit light comprises a bundle of optical fibers and at least one light guide.

7. Apparatus as claimed in a claim 1, wherein the means to transmit light includes a right-angle prism mounted such that its hypotenuse face is adjacent the back of the reflective surface of the second reflector.

8. Apparatus as claimed in claim 1, wherein one or more of the first, second and third reflectors comprises a right-angle prism.

9. Apparatus as claimed in claim 1, further comprising means to prevent rotation of the viewed image as the first reflector rotates about the rotation axis.

10. Apparatus as claimed in claim 9, wherein the image receiving means comprises an image-to-video conversion device which is mounted to rotate synchronously with the first reflector to prevent rotation of the viewed image.

11. Apparatus as claimed in claim 9, wherein the means to prevent rotation of the viewed image comprises a dove prism, a double dove prism or a Pechan prism.

12. Apparatus as claimed in claim 11, further comprising means to correct inversion of the image produced by the rotation preventing prism(s).

13. Apparatus as claimed in claim 12, wherein the means to correct inversion of the image comprises a dove prism, a double dove prism or a Pechan prism.

14. Apparatus as claimed in claim 1, wherein the apparatus is operable to provide a direction of view which is variable over a range of about 120°.

15. Apparatus as claimed in claim 1, wherein the means to transmit light comprises a bundle of optical fibers and at least one right-angle prism.

16. Apparatus as claimed in claim 15, wherein the means to transmit light includes three right-angled prisms.

17. Apparatus as claimed in claim 1 wherein said means to transmit light comprises three right-angled prisms.

18. Apparatus for use as a borescope or endoscope, comprising:

a tube having a proximal end and a distal end;

a viewing port at the distal end;

an optical train defining a longitudinal axis extending through the viewing port;

a first reflector having a reflective surface mounted at 45° to the longitudinal axis and laterally offset therefrom, and mounted for rotation about a rotation axis perpendicular to and intersecting the longitudinal axis and intersecting the center of the reflective surface;

a second reflector having a reflective surface mounted at 45° to the longitudinal axis and intersected by the longitudinal axis, such that light entering the viewing port is reflected by the first reflector to the second reflector and by the second reflector to the optical train;

a third reflector in the distal end of the tube, with said third reflector having a reflective surface mounted symmetrically about the longitudinal axis with respect to the first reflector and being rotatable synchronously with the first reflector about the rotation axis; and an optical fiber bundle which is positioned to transmit light to said third reflector in the distal end of the tube such that a viewed field of the first reflector is maintained illuminated while the third reflector rotates synchronously with the first reflector.

19. Apparatus as claimed in claim 18 further comprising means for redirecting light from the optical fiber bundle from a first direction to a second direction different than the first direction and extending along the longitudinal axis.

20. Apparatus for use as a borescope or endoscope, comprising:

a tube having a proximal end and a distal end;

a viewing port at the distal end;

an image-to-video conversion device defining a longitudinal axis extending through the viewing port;

a first reflector having a reflective surface mounted at 45° to the longitudinal axis and laterally offset therefrom, and mounted for rotation about a rotation axis perpendicular to and intersecting the longitudinal axis and intersecting the center of the reflective surface;

a second reflector having a reflective surface mounted at 45° to the longitudinal axis and intersected by the longitudinal axis, such that light entering the viewing port is reflected by the first reflector to the second reflector and by the second reflector to the image-to-video conversion device;

a third reflector in the distal end of the tube, with said third reflector having a reflective surface mounted symmetrically about the longitudinal axis with respect to the first reflector and being rotatable synchronously with the first reflector about the rotation axis; and an optical fiber bundle which is positioned to transmit light to said third reflector in the distal end of the tube such that a viewed field of the first reflector is maintained illuminated while the third reflector rotates synchronously with the first reflector.

* * * * *